United States Patent [19]

Selby et al.

[11] Patent Number: 5,503,002
[45] Date of Patent: Apr. 2, 1996

[54] SENSITIVE ROTATING VISCOMETER INSTRUMENT

[75] Inventors: Theodore W. Selby; Gregory C. Miiller, both of Midland; Michael A. Tubbs, Zeeland; Kevin J. Wolfe, Midland, all of Mich.

[73] Assignee: Tannas Co., Midland, Mich.

[21] Appl. No.: 336,287

[22] Filed: Nov. 8, 1994

[51] Int. Cl.$^6$ .............................. A23G 9/00; G01N 11/14
[52] U.S. Cl. ...................... 73/54.28; 73/54.35; 73/54.12
[58] Field of Search ................................ 73/54.28, 54.35, 73/54.29, 54.31, 54.33, 54.12, 54.28, 54.35, 54.29, 54.31, 54.33, 54.12

[56] References Cited

U.S. PATENT DOCUMENTS

| | | | |
|---|---|---|---|
| 2,553,844 | 5/1951 | Buchdahl et al. | 73/59 |
| 3,053,078 | 9/1962 | Jewett | 73/54 |
| 4,648,263 | 3/1987 | Deysarkar et al. | 73/59 |
| 5,095,710 | 3/1992 | Black et al. | 62/68 |

FOREIGN PATENT DOCUMENTS 0231873  8/1987  European Pat. Off. .............. 73/54.35

OTHER PUBLICATIONS

Ser. No. 08/308918 Filed Sep. 20, 1994 "Rotor–Stator Adapter for Sensitive Rotating Viscometers".
ASTM D 5133-90 (1990).
Tannas Catalog, p. 4 (Plus Eight) & 5 (Plus Two), 1992.
Lubricant World (Plus Four), 1992.
Brookfield Rheolog Laboratory Viscometer Bulletin for Catalog, Page RL–100, 1970.
C. W. Brabender Instruments Catalog, pp. 1–4, 1966, (Plastograph Instrument Design/Viscosity).

Primary Examiner—Hezron E. Williams
Assistant Examiner—J. David Wiggins
Attorney, Agent, or Firm—Christopher John Rudy

[57] ABSTRACT

A sensitive rotating viscometer instrument generally having a housing surrounding a bath tub, the housing having a top upon which can be provided at least one sensitive rotating viscometer with a stator insertable through the top of the housing and into the bath, and which head remains above the top of the housing, includes at least one of the following features:

(A) a conduit for supply of dry gas, extending under the top of the housing in a concealed or inconspicuous manner to couple near the viscometer head, for a dry gas blanket over the fluid to be tested in the stator;

(B) an ergonomically positioned panel to include for at least one of the following: dry gas, power, and data transmission line control(s), coupling(s) and data display terminal(s) at highly visible, line of sight, and easily accessible position(s) above the top of the housing;

(C) an offset viscometer head arrangement in which the locations of viscometer heads form symmetrically offset, non-rectangular rows or columns in an array when plural viscometer heads are presentable in the instrument; and (D) an irregularly-shaped bath tub.

8 Claims, 7 Drawing Sheets

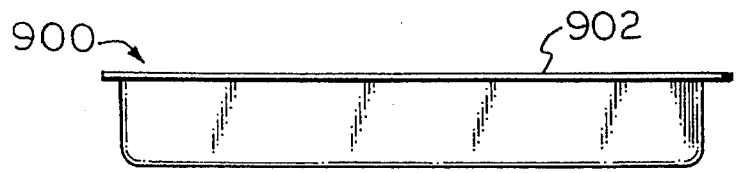
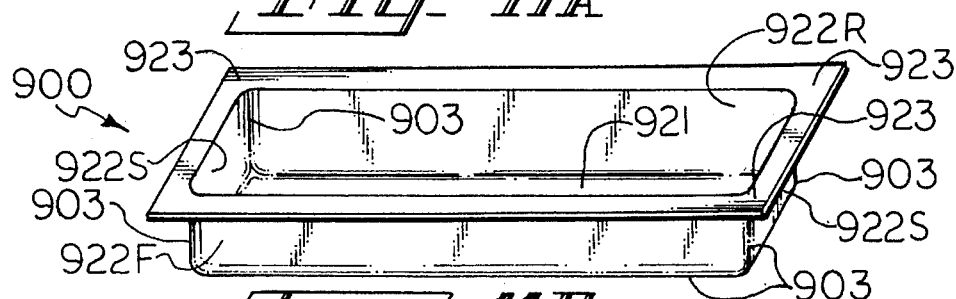
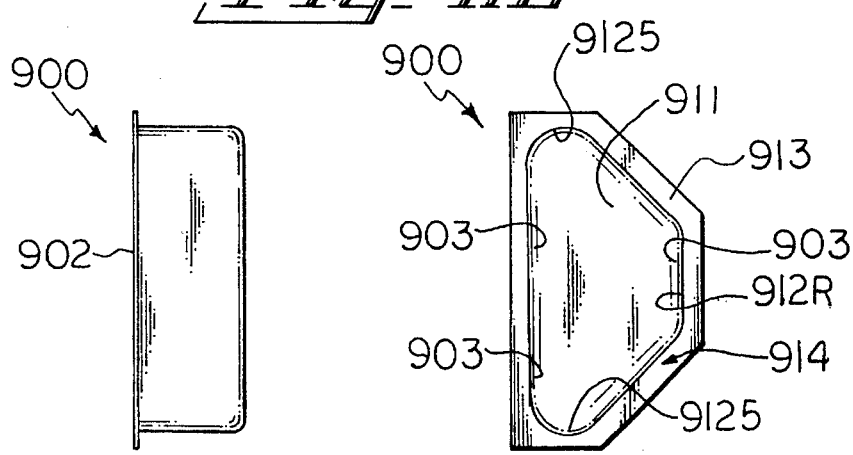
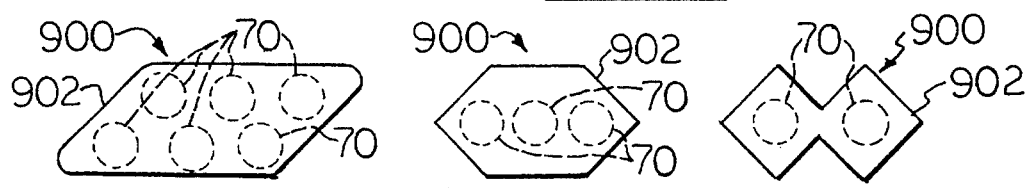
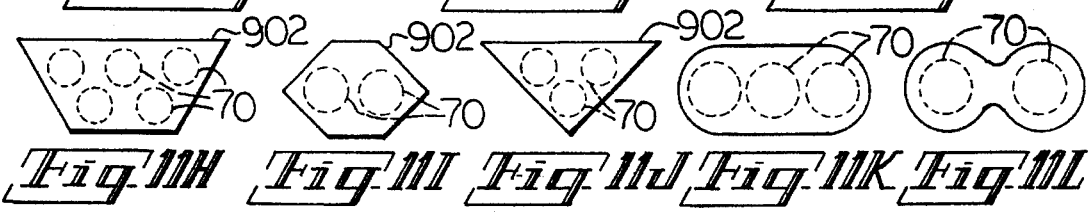

SENSITIVE ROTATING VISCOMETER INSTRUMENT

FIELD

The present invention concerns sensitive rotating viscometer instruments. It especially concerns Brookfield viscometers useful in the Scanning Brookfield Technique.

BACKGROUND

In 1981, Mr. Theodore W. Selby developed the now well-known Scanning Brookfield Technique for determining viscosity values of fluid samples to especially include non-Newtonian liquids. This technique, licensed to the Tannas Co., Midland, Mich., is used in ASTM D 5133, incorporated herein by reference as its 1990 version.

Since then, rotating viscometers have been employed in this and other techniques, among which viscometers may be mentioned those available commercially from the Tannas Co. the former "Scanning Brookfield Plus Eight", "Scanning Brookfield Plus Four" and "Scanning Brookfield Plus Two" models. However, these and other Brookfield viscometers have had some vexing drawbacks of long standing duration.

For example, to obtain reliable results and protect both test sample integrity and components of the viscometer, such sensitive rotating viscometer instrumentation requires a dry gas blanket over the test fluid residing in the viscometer stator component, which is immersed in a bath of temperature regulating liquid such as, for example, methanol. See e.g., Deysarkar et al., U.S. Pat. No. 4,648,263, incorporated herein by reference. To provide dry gas, supply lines such as of TYGON tubing were set up between regulators and viscometer head supporting apparatus. Such tubing, although serving a necessary purpose, was susceptible to crimping, kinking, breaking or becoming disconnected by operator accident, thus impairing the supply of dry gas for the blanket. Moreover, tubing could come into contact with solvents spilled on the heavy-viscometer-head-supporting and bath-protecting housing top, thus becoming susceptible to deterioration therefrom, plus becoming a vehicle for the undesirable transmission of the solvents to personnel operating the instrument or to other locales. Also, such an arrangement was unsightly.

In addition, controls were frequently placed on the top of the housing, engendering increased possibilities of contact with solvents from not only dry air supply lines but also power and data transmission lines, as generally outlined above, thus providing problems from deterioration of lines and from operator-solvent or other contact as could so follow. Also, control panels, if any were present on the instrument such as found in some labs on the rear of the larger, floor models, were provided at awkward heights, and inadequately provided for effective control and monitoring of set-up and test operations.

Furthermore, as understood at the time to be the most efficient arrangement of components, viscometer heads were lined up in straight rows, with instruments having multiple rows of heads having their heads lined up in columns at right angles to the front row of heads. A bath stirring motor was placed to the side of the row(s) of heads. The bath tub was made with a rectangular or square top profile to correspond thereto. Such an arrangement, however, was not without its problems. Operator access to the heads was constrained and could be frustrating as it was difficult to see readings on the front face of the viscometer heads in the rear row, plus difficult to service the front row dry gas supply lines and couplings, and power and data transmission lines and couplings, which couplings are typically in the rear of head support devices and heads, in addition to those for the rear row of heads.

In addition to solutions to problems such as set forth above and otherwise present in the art, increased efficiency and lowered cost of operation are always sought after. What is needed accordingly is rotating viscometer instrumentation which ameliorates or solves such problems and advances the art. A prime goal is the easy and effective use thereof, to especially include, by even inexperienced operators.

SUMMARY

The present invention provides, in a sensitive rotating viscometer instrument having a housing surrounding a bath tub for holding a bath of liquid for controlling temperature of at least one test sample fluid for viscosity testing, the housing having a top, upon which can be provided a sensitive rotating viscometer with a head in which is a motor for driving a rotor fixable to a lower end of the viscometer and rotatable about an axis of rotation by the motor in a predetermined quantity of a test fluid present in a tube-like stator closed at a distal, bottom end thereof and attachable to the head at a proximate, top end thereof, which stator, containing test fluid surrounding the rotor and directly or indirectly attached in conjunction with the test fluid and rotor to the viscometer, is insertable through the top of the housing and into the bath, and which head remains above the top of the housing, the rotor being rotatable about its longitudinal axis by the viscometer motor and cooperating with the stator and fluid to create drag related to the viscosity to be measured by the viscometer, improvement(s) comprising:

(A) a conduit for supply of dry gas, extending under the top of the housing to couple near the viscometer head, for a dry gas blanket over the fluid to be tested in the stator;

(B) an ergonomically positioned panel to include for dry gas, power, and/or data transmission line control(s) and/or coupling(s) and/or data display terminal(s) at position(s) above the top of the housing;

(C) an offset viscometer head arrangement when plural viscometer heads are presentable in the instrument; and/or (D) an irregularly-shaped bath tub.

The invention is useful in measuring viscosities with sensitive rotating viscometers, especially Brookfield viscometers. It can be particularly useful in plural-headed viscometers useful in the Scanning Brookfield Technique.

Significantly, by the present invention, problems of the prior art are ameliorated or eliminated. Dry gas supply lines are protected within the housing, thus addressing problems of the prior art associated with major lengths of exposed tubing, and providing cleaner, more desirable and efficient operation. Controls and monitors are amply and ergonomically presented, above the top of the instrument, thus addressing problems of the prior art associated with housing-top-positioned and/or inadequate controls or display. Heads are offset for ready access for coupling and observation, addressing problems of the prior art associated with inaccessibility for coupling and monitoring. Efficiency is increased by the tub layout. The article of the invention is easily and effectively used, especially by even inexperienced operators. Customers and users alike are pleased with the invention.

Numerous further advantages attend the invention.

DRAWINGS IN BRIEF

The drawings form part of the specification hereof.

In the herewith presented drawings, where like numerals refer to like features in the instant specification, note:

FIGS. 11A, 11B, 11C, 11D, 11E, 11F, 11G, 11H, 11I, 11J, 11K and 11L are side, perspective and top views of tubs hereof.

ILLUSTRATIVE DETAIL

Figure 1:
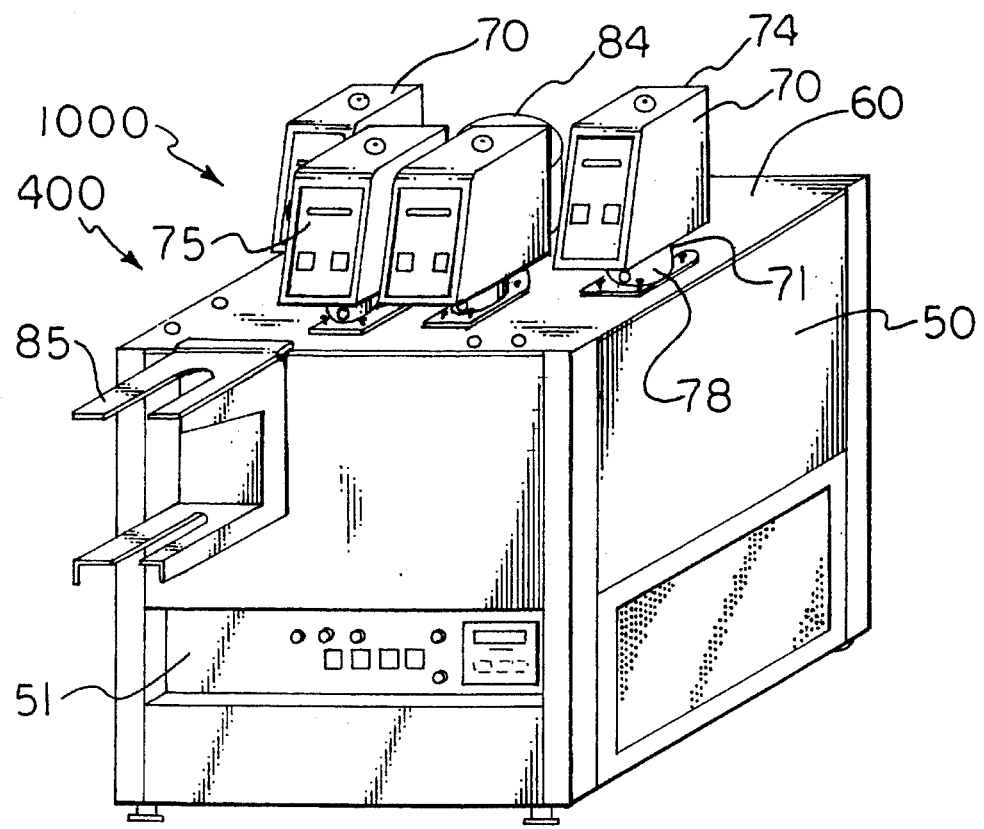
FIG. 1 is a right perspective view of an embodiment of the invention.
Figure 2:
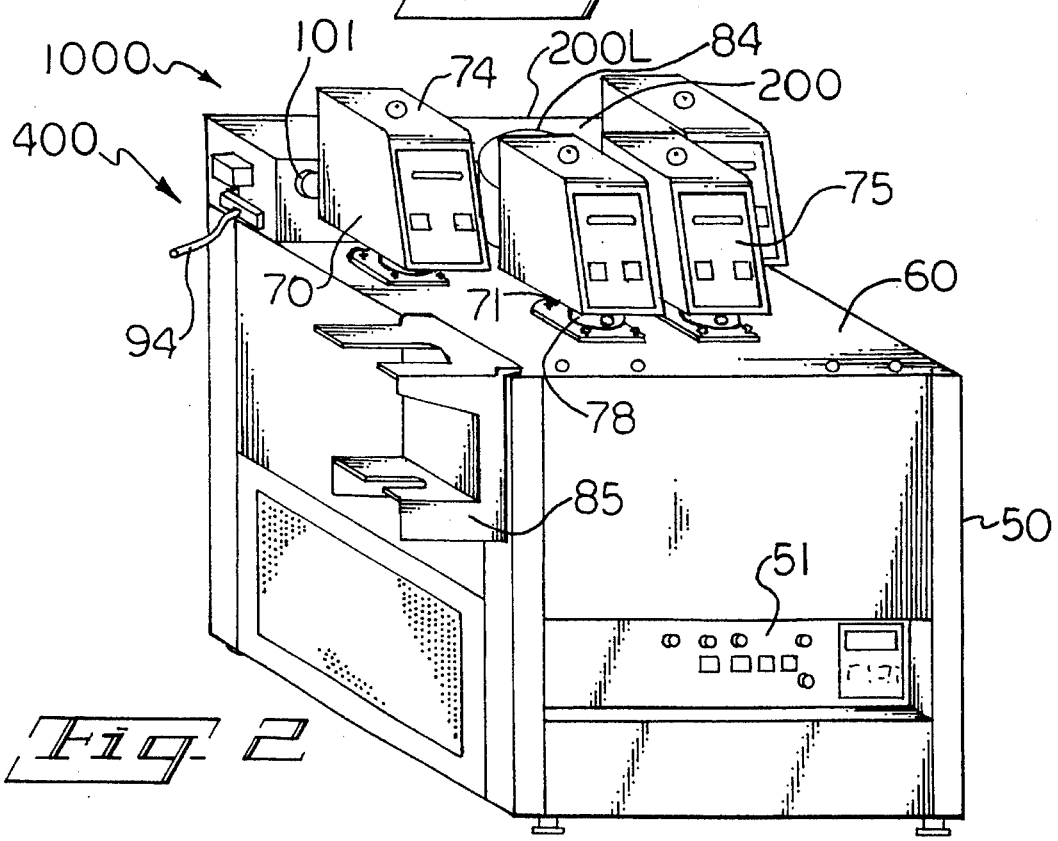
FIG. 2 is a left perspective view thereof.
Figure 3:
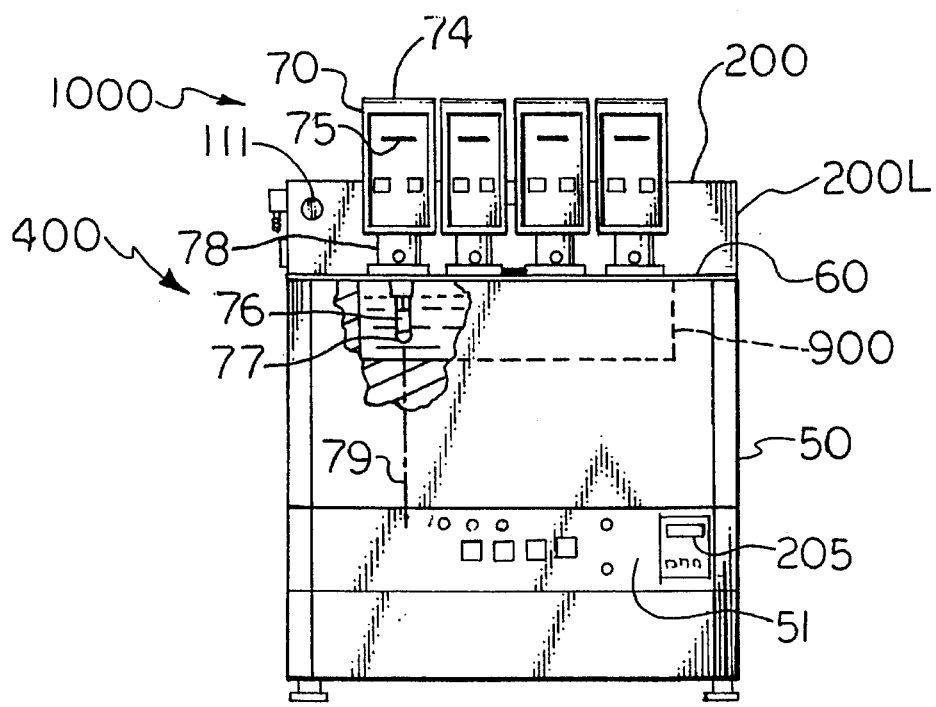
FIG. 3 is a front view thereof.
Figure 4:
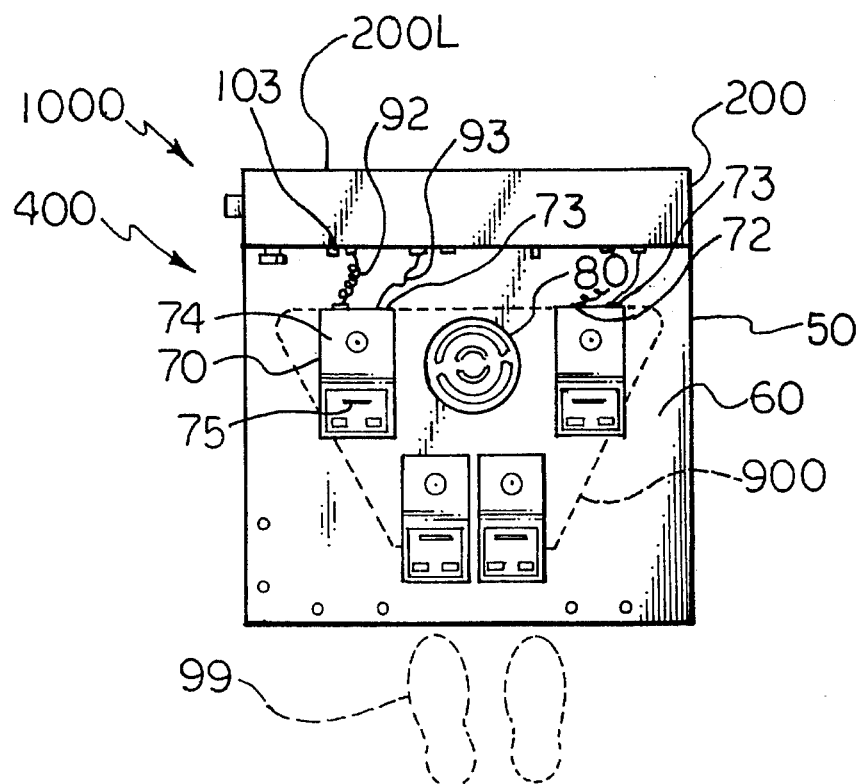
FIG. 4 is a top plan view thereof.
Figure 5:
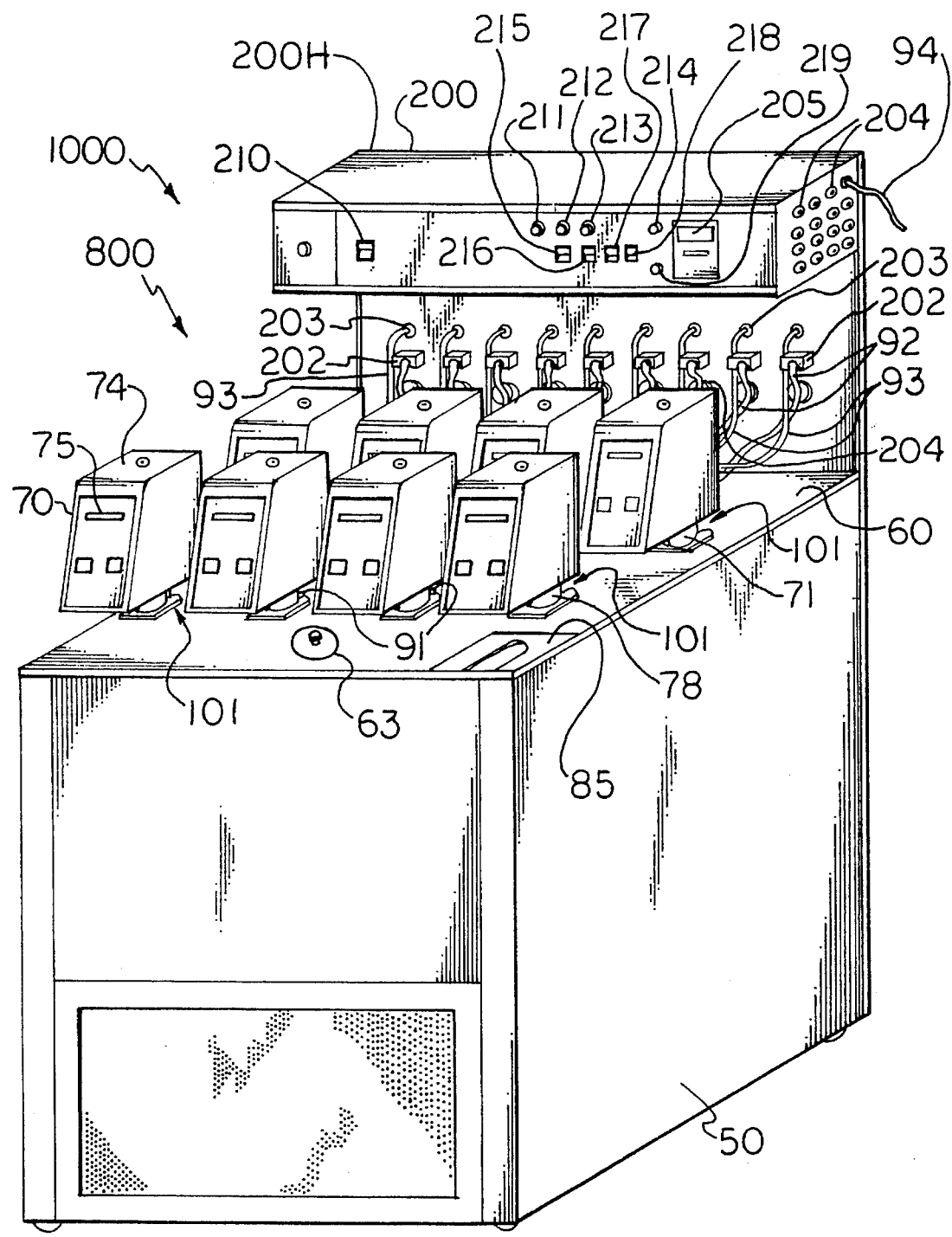
FIG. 5 is a right perspective view of another embodiment of the invention.
Figure 6:
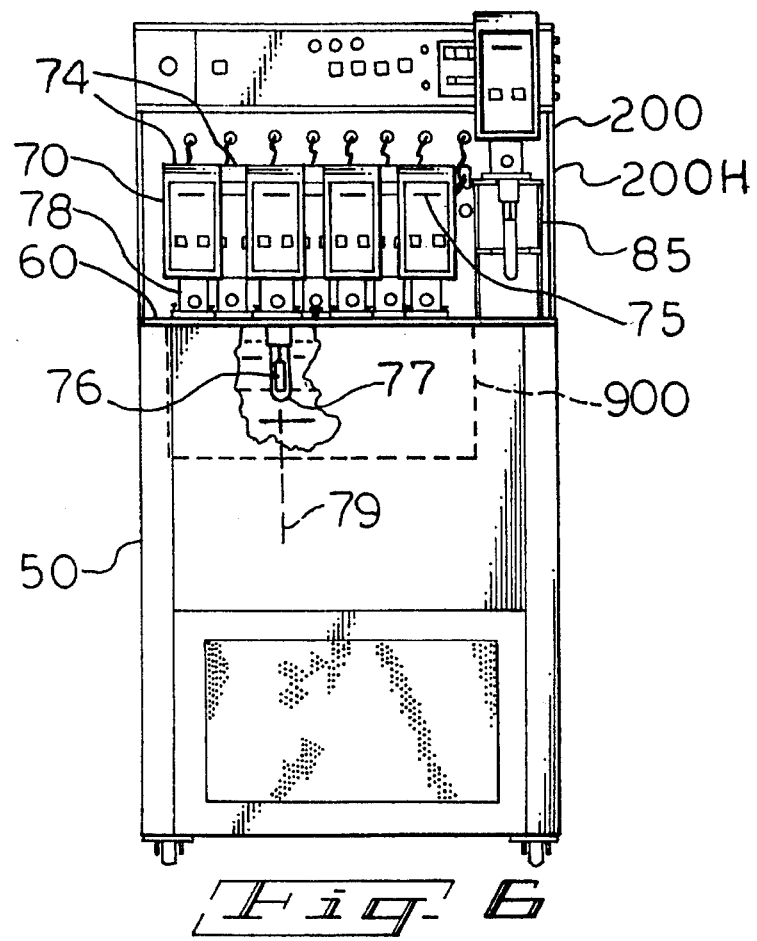
FIG. 6 is a front view thereof.
Figure 7:
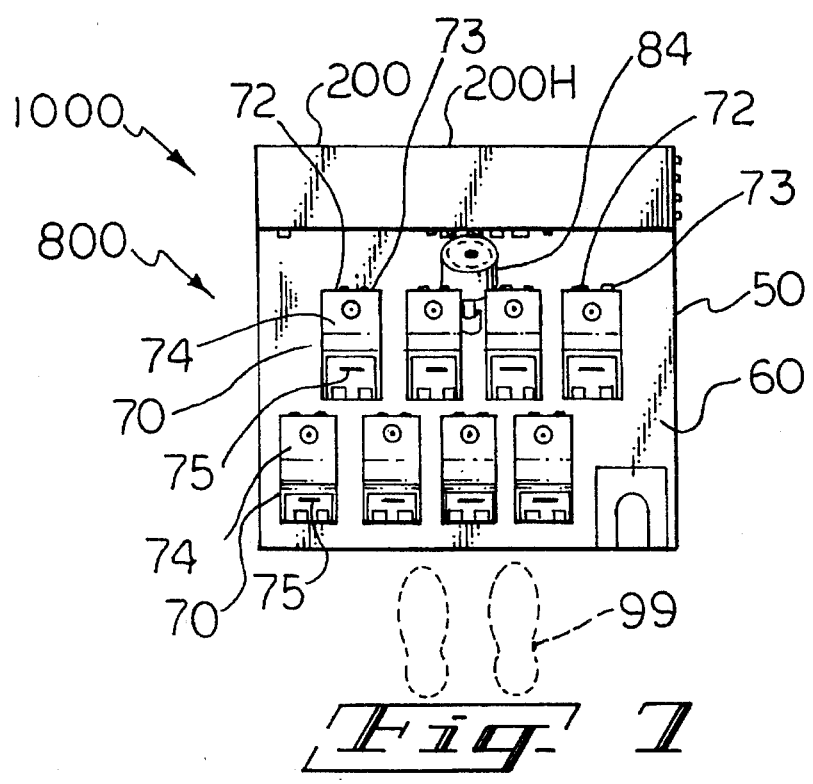
FIG. 7 is a top plan view thereof.

In reference to the drawings, sensitive rotating viscometer instrument 1000 has housing 50 with top 60, and viscometer 70 has a dry gas coupling 71. Power coupling 72, and data transmission coupling 73 are on viscometer head 74, which has viscometer head data display panel 75. Rotor 76, rotated by a motor inside the viscometer head, stator 77, and collar housing 78 are present. Preferably, the collar housing/interior stator collar assembly is such as disclosed by Van Meter et al., U.S. patent application Ser. No. 08/308,918 filed Sep. 20, 1994, incorporated herein by reference, to include with generally rectangular plate (143). Rotor 76 and stator 77 are concentric with axis of rotation 79.

In general, also with instrument 1000, compressor 80, dry gas supply 81, temperature regulating apparatus 82, and insulated cooling line 83 are present. Other components are also generally present in the housing 50. A motor-driven bath stirrer 84 and viscometer assembly stand 85 can be present. External power source line 90 is provided to deliver suitable electric power to run the instrument. Dry gas supply tubing 91, viscometer head power line 92, viscometer head data transmission line 93, and/or external data transmission line 94 such as, for example, connected to an external computer, are generally present.

Conduit 100 for supply of dry gas extends under top 60 and runs to coupling 101 near where viscometer 70 can be emplaced with its head 74 above the top 60 for testing. This can supply dry gas for a blanket over the fluid to be tested in stator 77. Preferably, the conduit 100 runs in a channel 102 provided in a sub-top 103 attached to top 60. Control 111 regulates dry gas flow from dry gas supply 81 for the blanket.

Conduit 100 can be of any suitable substance, to include inert plastics, metals, and other compositions impervious to the dry gas, which is typically dry air or nitrogen. It is preferably of copper.

Top 60, especially as a component in such a configuration, can be made of any suitably stiff, strong, solvent resistant, colorfast, scratch resistant, machinable, self-extinguishing material, optionally with fair passive thermal insulative properties. Suitable top materials accordingly may include stainless steel and treated thermoplastics such as acrylic-polyvinylchloride alloys, for example, of ¼-inch KYDEX-100 acrylic-polyvinylchloride alloy. Sub-top 103, especially as a component in such a configuration also, can be made of any suitably stiff and strong, usually more stiff and strong than top 60, solvent resistant, high moisture resistant, high temperature resistant, readily machinable material, typically with good passive thermal insulative properties. Suitable sub-top materials accordingly may include phenolic composites laminated with canvas, linen, glass fiber, and/or paper, for example, of ¼-inch GAROLITE grade XX paper-laminated phenolic. Sub-top 103 can be cut to be in general registry with the bath tub perimeter, and its attachment to the top can include by gluing. The conduit 100 can be coated with a sealer when it is placed in the channel 102. The coupling 101, typically of brass, may also be of nylon, polyethylene, polytetrafluoroethylene, or other suitable material.

With models having the conduit 100 under the top 60 such as, for example, in larger models, an operator need only affix a short length of tubing 91 at couplings 71 and 101 to complete a passageway for the dry gas supply. The short length of tubing is found to retain its integrity very well, with unimpeded gas flow, while, being shielded by the viscometer head, providing a minimal target for accidental contact. Thus, dry gas supply lines are substantially contained, and a cleaner, more desirable and efficient instrument with its operation is provided. Otherwise, a coupling 103 may be on a raised panel 200 such as on a low panel 200L found in bench top instruments. Tubing 91 is connected to couplings 71 and 103 for dry gas.

The raised panel 200 may be present on instrument 1000. It may be ergonomically positioned about eye level, as, for example, in larger, floor model instruments by substantially high panel 200H, or in more compact, bench top instruments by the low panel 200L, which include at least one of the following features at position(s) above the top of the housing 60: dry gas control 201; viscometer head power line coupling 202; viscometer head data transmission line coupling 203; external data transmission line coupling 204; data display terminal 205. Feature(s) such as the foregoing may be on a front panel 51 of the housing 50 as in a smaller instrument. In addition, on the front panel 51 or on upraised panel 200, for example, on high panel 200H as in a larger, floor model instrument, added feature(s) may be present to include as follow: power switch/indicator light 210; high temperature cut-out indicator light 211; cooling indicator light 212; heating indicator light 213; low bath liquid level indicator light 214; manual/automatic cooling switch/indicator light 215; manual/automatic heater switch/indicator light 216; stirrer on/off switch/indicator light 217; programmer on/off switch/indicator light 218; very low bath liquid automatic safety shutdown indicator light 219. In cooperation with such features, suitable useful sensors, heating/cooling apparatus, a stirrer, etc., are provided and are in communication therewith so that an operator can conveniently control and monitor the instrument and its status during set-up, testing and shut-down. With raised panel 200 such as the low panel 200L and especially the high panel 200H, an operator can readily adjust the flow of dry gas with control 201, connect viscometer head power line 92 between couplings 72 and 202, viscometer head data transmission line 93 between couplings 73 and 203, connect external data transmission line between coupling 204 and a suitable external recording device, and monitor the set-up, testing and take-down with the instrument 1000. A computer output port can be provided on the raised panel 200.

Thus, the couplings, controls and monitors are amply and ergonomically presented above top 60 of instrument 1000. And so, supply and transmission lines can be far less prone to contamination such as from spilled solvent on the top of the instrument and can be readily installed and taken down, and the display of data, the control of test components, and the monitoring of testing is also significantly improved.

Instrument 1000 may have an offset viscometer head arrangement when plural viscometer heads 74 are able to be present therewith, in particular with instruments having three or more heads, each viscometer 70 being emplacable through the top 60 in a viscometer stator hole 67, with the top 60 generally further having a bath liquid filler hole 62 and plug 63, and bath stirrer access hole 64. Such orifices pass through the sub-top 103 as well. In reference to the head arrangement, by the term "offset" is meant, most generally, that row(s) or column(s) of positions available for the heads 74 are not parallel or perpendicular to front 61 of the top 60 of the instrument 1000 or to a standard position of an operator 99 facing it.

Thus can be provided, for instance, a winged-head arrangement such as, for example, with the 4-headed "Scanning Brookfield PlusFour" model viscometer 400, or a staggered-head arrangement such as, for example, with the 8-headed "Scanning Brookfield PlusEight" model viscometer 800, both new and available from the Tannas Co. The heads 74 can be arranged in offset fashion and accommodate placement of the bath stirrer 84 and viscometer assembly stand 85, which may be of the movable hanging variety (PlusFour) or the pop-up variety (PlusEight) and so forth.

Thereby, ready access for coupling of the heads 74 and observation of their data display panels 75 is provided. Moreover, connected lines can avoid the confusing complication of becoming entangled, and unsightly, and set-up is a less cumbersome procedure thereby. Such provides significant advances in operator usability.

Figure 8:
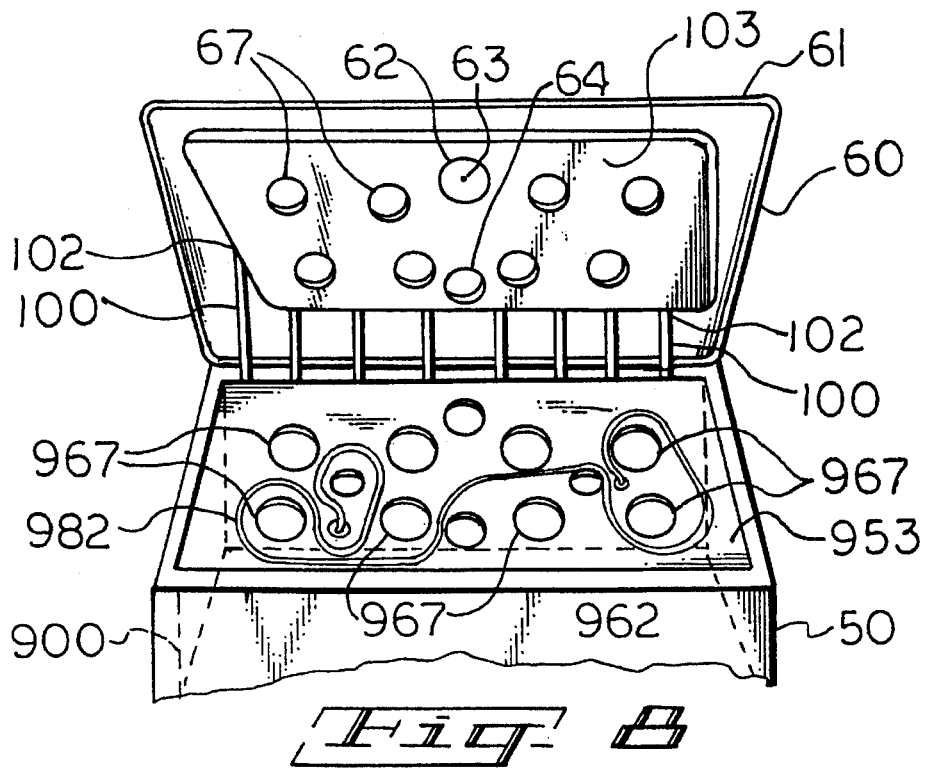
FIG. 8 is a front view thereof with the top opened.
Figure 9:
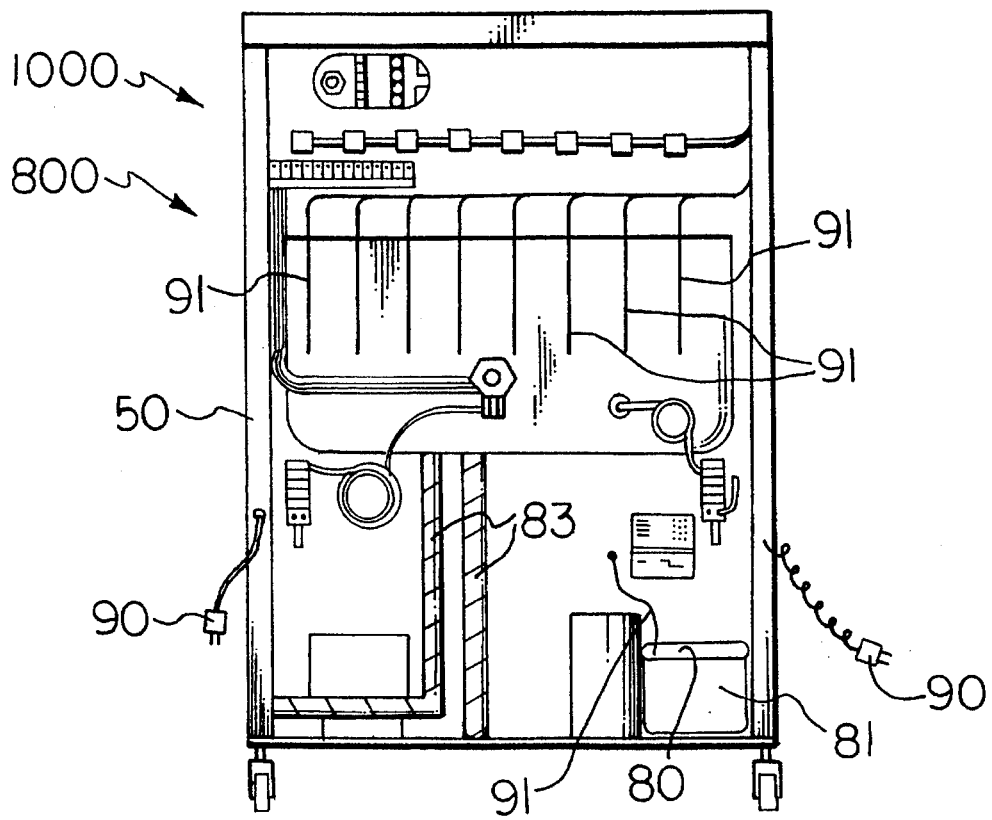
FIG. 9 is a rear view thereof with a back panel removed.
Figure 10A:
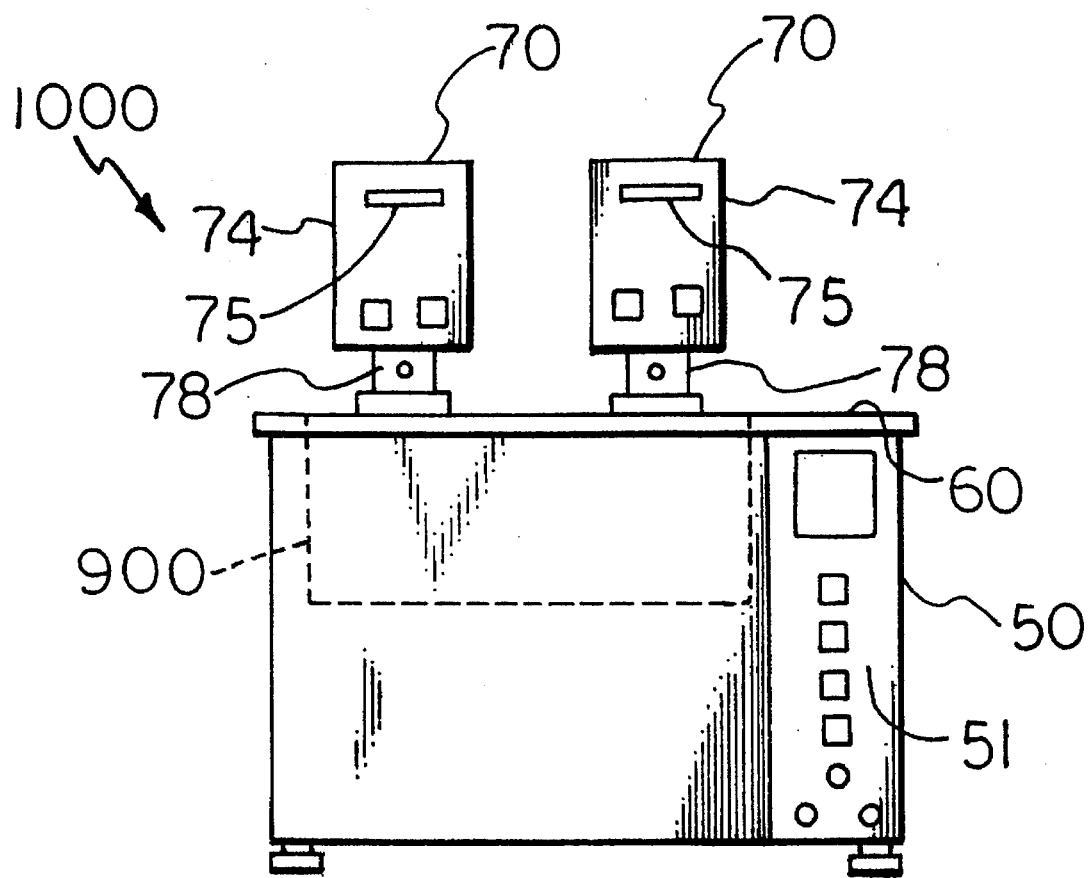
FIGS. 10A and 10B show front and top views of another embodiment thereof.
Figure 10B:
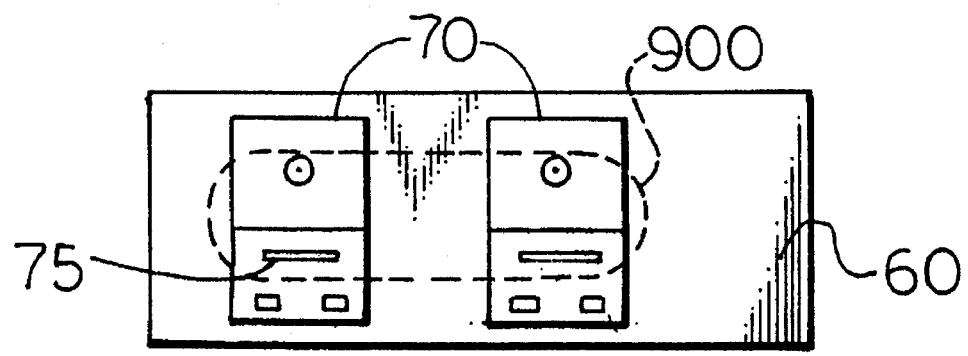

Instrument 1000 may have irregularly-shaped bath tub 900. In reference to the bath tub shape, by "irregularly" is meant a shape which is, in general, not cylindrical, cubic, a square-bottomed box, nor a rectangularly-bottomed box. Accordingly, irregularly shaped tubs include those with top view profiles of acircular curvilinear shape or truncated curvilinear shape such as, for example, an ellipse having two separate foci; a non-elliptical oval; a figure-8 communicating one distended part to the other with an arced midsection; a circle truncated by a chord, to include a semicircle; a circle truncated by a plurality of chords, e.g., by two parallel equilinear chords; an ellipse truncated by at least one chord; a non-elliptical oval truncated by at least one chord; and with top view profiles of angular geometric figures such as, for example, a triangle; a rhombus; a rhomboid, i.e., an obliquely-angled parallelogram; a regular trapezoid, i.e., a trapezoid equiangular on both ends of an unequal side; irregular trapezoids; a trapezium; pentagons; hexagons to include ones which have an opposing pair of sides longer than the other sides; heptagons; octagons to include ones with an angularly bounded figure-8 with generally quadrilateral outside boundary distended parts communicating with each other through an aperture defined by two points; nonagons; decagons; dodecagons, to include ones with an angularly-bounded figure-8 with generally pentagonal outside boundary distended parts communicating with each other through a bi-linearly-bounded middle section; and so forth and the like, and combinations thereof.

Thus, for example, bath tub 900 with an open-topped regular trapezoid bottomed box with sides normal thereto, or with an open-topped parallelepiped with sides normal to its non-normal-angle-sided bottom, can be provided.

Tubs 900 are made to contain a liquid, for example, methanol, which regulates the temperature of the fluid being tested in stator 77, which is typically of glass. Commonly, the tub 900 is made of stainless steel.

A tub 900, for example, can be about 6-½ inches deep, with a 10-gauge (ca. ⅛-inch) stainless steel bottom 901 and 18-gauge (ca. 1/20-inch) stainless steel walls 902 with rounded "corner" connections 903. As an illustration, with 1-½-inch radius "corners" trapezoidal bottom 911 is attached to 5-½-inch rear wall 912R (measured to radius, hence about 8-½ inches to imaginary vertex 913), two side walls 913S, and 15-inch front wall 912F (measured to the radius, hence about 18 inches to imaginary vertex 913) to provide for a trapezoid height, i.e., front to back distance, of some 9-¼ inches, with a 1-inch flange 914 attached to the outside perimeter of the tub on the upper end of the walls, 912F, 912R and 912S, the walls attached together to include the rounded "corner" connections 903. As another illustration, with 1-½-inch radius "corners" parallelogram bottom 921 is attached to 21-inch front wall 922F and rear wall 922R (measured to radius, hence about 24 inches to imaginary vertex 923) and two side walls 922S at an acute angle of about 68 degrees (corresponding obtuse angle of about 112 degrees) to provide for a parallelogram height, i.e., front to back distance, of some 12 inches, with a 1-inch flange 924 attached to the outside perimeter of the tub on the upper end of the walls, 922F, 922R and 22S, the walls attached together to include the rounded "corner" connections 903. The bottom 901 and walls 902 are attached to one another with a continuous hydraulic weld, and the flange 904 is attached with a continuous weld.

In assembling a bath such as irregularly-shaped bath tub 900 with instrument 1000, a tub top 953 is employed. Tub top 953 is generally strong enough to support the sub-top 103 and top 60 with viscometers 70 thereon. Thus, the tub top 953, especially as a component in the irregularly-shaped bath tub containing instrument, is made of a suitably quite stiff, strong, solvent resistant, high moisture resistant, high temperature resistant, readily machinable material, typically with good passive thermal insulative properties. Suitable tub top materials accordingly include the phenolic composites laminated with canvas, linen, glass fiber, and/or paper, for example, of the ¼-inch GAROLITE grade XX paper-laminated phenolic. Tub top 953 can be cut to be in general registry with the bath tub perimeter and flange, and it may be attached thereto to include by gluing. Supports 960 are preferably positioned within the perimeter of the tub top 953 so as to provide support for the top 60 through the sub-top 103. Generally cut in the tub top, and top insulation layer, are bath tub filling hole 962, bath stirrer access hole 964, and viscometer insertion holes 967.

The bath 900 is insulated. Suitable insulation should be able to provide an effective thermal barrier for the low temperature contents of the bath and be suitably chemically and/or thermally resistant. For example, insulation of the sides of the tank can include some 1-½ to 4 inches of a rigid R-board insulation such as ATLAS FIBER BOARD insulation (R-value about 5.2) and of the bottom of the tank at least 4 inches of such insulation as the ATLAS FIBER BOARD. Insulation of the top of the tank can be provided by suitable closed cell skinned foams such as of polyethylene or polyvinylchloride as found with a ¼-inch layer of a 2-pound per cubic foot density, closed celled, foamed polyethylene, for example, VOLARA foam sheets (thermal conductivity rating 0.25 BTUs per inch; high temperature rating 180 degree F.), or with a ¼-inch layer of a 6-pound per cubic foot, closed celled, foamed polyvinylchloride, for example, FLEX-SULATION foam sheets (thermal conductivity rating 0.26 BTUs per inch; high temperature rating 220 degrees F.). On top of the tub top top insulation can be a heater 982, which helps insure that condensation does not form on the underside of the sub-top 103. Although the FLEX-SULATION foam sheet does not have as good a thermal conductivity rating as the VOLARA, it has better high temperature characteristics, which can be significant when employing the heater 982.

Thereby, with such an irregularly-shaped bath 900, a reduced volume of bath liquid can be employed. This reduces the cost of operation due to cost of the liquid, provides for easier cooling and heating, and may reduce the surface area to volume ratio of the bath liquid, which can lessen the amount of the liquid, for example, methanol, lost by evaporation, and lessen the rate of undesired water uptake of the methanol from atmospheric water. In addition, such a bath permits increased use of insulation within housing 50, which typically has a rectangular top profile, and therefore, even though there may be a larger tub side wall surface area in relation to tub volume, thermal heat loss can be minimized. Accordingly, the effective use of smaller compressors and a reduced use of ozone-depleting refrigerants are possible.

The instrument can be employed to measure viscosities of fluids over broad temperature ranges as is known in the art. It is particularly useful within the range of from about 0 degrees C., to about minus 50 degrees C., especially to include from about minus 4 degrees C., to about minus 40 degrees C., can be employed to study the critical degree of gelation of lubricants at low temperatures, and can be used in other tests, as those skilled in the art appreciate.

We claim:

1. In a sensitive rotating viscometer instrument having a housing surrounding a bath tub for holding a bath of liquid for controlling temperature of at least one test sample fluid for viscosity testing, the housing having a top, upon which can be provided at least one sensitive rotating viscometer with a head in which is a motor for driving a rotor fixable to a lower end of the viscometer and rotatable about an axis of rotation by the motor in a predetermined quantity of a test fluid present in a tube-like stator closed at a distal, bottom end thereof and attachable to the head at a proximate, top end thereof, which stator, containing test fluid surrounding the rotor and directly or indirectly attached in conjunction with the test fluid and rotor to the viscometer, is insertable through the top of the housing and into the bath, and which head remains above the top of the housing, the rotor being rotatable about its longitudinal axis by the viscometer motor and cooperating with the stator and fluid to create drag related to the viscosity of the test fluid in the stator to be measured by the viscometer, improvement(s) comprising at least one of the following:

(A) a conduit for supply of dry gas, extending under the top of the housing in a concealed or inconspicuous manner to couple near the viscometer head, for a dry gas blanket over the fluid to be tested in the stator;

(B) an ergonomically positioned panel to include for at least one of the following: dry gas, power, and data transmission line control(s), coupling(s) and data display terminal(s) at highly visible, line of sight, and easily accessible position(s) above the top of the housing;

(C) an offset viscometer head arrangement in which the locations of viscometer heads are geometrically displaced to form symmetrically offset, non-rectangular rows or columns in an array when plural viscometer heads are presentable in the instrument; and (D) an irregularly-shaped bath tub thereby excluding cylindrical-shaped forms, cubic-shaped forms, square-bottomed boxes and rectangular-bottomed boxes, where said bath tub has a top-view profile comprising a polygon shape, an acircular curvilinear shape, a truncated curvilinear shape, or any combination thereof.

2. The instrument of claim 1, wherein at least three viscometers with heads are presentable, and the offset viscometer head arrangement and the irregularly-shaped bath tub are present.

3. The instrument of claim 2, wherein the viscometer head arrangement is in a winged formation arrangement, and the irregularly-shaped bath tub has a top view profile of a trapezoid-shaped perimeter.

4. The instrument of claim 3, wherein four viscometers with heads are presentable.

5. The instrument of claim 2, wherein the viscometer head arrangement is in a staggered arrangement, and the irregularly-shaped bath tub has a top profile in general of a non-right-angled parallelogram.

6. The instrument of claim 5, wherein eight viscometers with heads are presentable.

7. The instrument of claim 2, wherein said conduit extends under the top of the instrument.

8. The instrument of claim 6, wherein said conduit which extends under the top of the instrument is present.

* * * * *